United States Patent
Mioskowski et al.

(10) Patent No.: US 8,158,784 B2
(45) Date of Patent: Apr. 17, 2012

(54) QUINUCLIDINE DERIVATIVE USEFUL IN THE PREPARATION OF MEQUITAZINE

(75) Inventors: Charles Mioskowski, Strasbourg (FR); Vanessa Gonnot, Suce en Erdre (FR); Rachid Baati, Souffel Weyersheim (FR); Marc Nicolas, Gaillac (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 162 days.

(21) Appl. No.: 12/523,249

(22) PCT Filed: Jan. 17, 2008

(86) PCT No.: PCT/FR2008/000056
§ 371 (c)(1),
(2), (4) Date: Dec. 15, 2009

(87) PCT Pub. No.: WO2008/107545
PCT Pub. Date: Sep. 12, 2008

(65) Prior Publication Data
US 2010/0105897 A1    Apr. 29, 2010

(30) Foreign Application Priority Data
Jan. 18, 2007   (FR) ...................................... 07 52742

(51) Int. Cl.
*C07D 453/02*   (2006.01)
*C07D 417/14*   (2006.01)

(52) U.S. Cl. ............................. 544/31; 544/43; 546/133
(58) Field of Classification Search .................... 544/31
See application file for complete search history.

(56) References Cited

U.S. PATENT DOCUMENTS

| 4,467,095 A | 8/1984 | Treves et al. |
| 4,937,239 A | 6/1990 | Lauffer et al. |

FOREIGN PATENT DOCUMENTS

| EP | 0 089 860 A1 | 9/1983 |
| EP | 1 074 552 A2 | 2/2001 |
| EP | 1 074 552 B1 | 10/2002 |
| FR | 2.034.605 A | 12/1970 |
| FR | 2 522 660 A1 | 9/1983 |
| FR | 2 777 278 A1 | 10/1999 |
| JP | 60-258187 A | 12/1985 |
| JP | 4-169583 A | 6/1992 |
| JP | 5-140157 A | 6/1993 |
| WO | WO-99/29692 A1 | 6/1999 |

*Primary Examiner* — Kahsay T Habte

(74) *Attorney, Agent, or Firm* — Birch, Stewart, Kolasch & Birch, LLP.

(57) ABSTRACT

The invention relates to a 1-aza-bicyclo[2.2.2]oct-2-en-3-yl-methyl acetate of the formula (I), wherein said compound is useful as a synthesis intermediate for the production of mequitazine.

4 Claims, No Drawings

QUINUCLIDINE DERIVATIVE USEFUL IN THE PREPARATION OF MEQUITAZINE

This invention relates to a new process for the preparation of mequitazine: 10-[1-aza-bicyclo(2,2,2)oct-3-yl]-methyl-10H-phenothiazine.

Mequitazine is a compound used as anti-histamine medication in the treatment of allergies. Its chemical structure and therapeutic activity are described in patent FR-0 064 605. Its levorotatory isomer is described in patent FR-2 522 660 and EP-089 860. The process for the preparation of mequitazine and its levorotatory isomer is also described in these patents. The latter presents a number of disadvantages.

Low-yield synthesis is carried out by alkylation of 3-(chloromethyl)quinuclidine and the sodium or potassium salt of phenothiazine in an inert solvent with a high boiling point such as xylene, with the addition of a co-solvent such as toxic HMPT, if need be. Another disadvantage is related to the use of sodium amide, which leads to substantial release of gaseous ammonia.

The reaction is not clean and a large number of by-products are produced. In particular, the product of HCl elimination from 3-(chloromethyl)quinuclidine into 3-(methylene)quinuclidine is formed under these reaction conditions, leading to a loss of yield.

Secondary products are also formed when the phenothiazine anion is produced, whether with sodium amide, sodium hydride, potassium tertiobutylate, etc. Intense coloration of the reaction medium indicates delocalisation of the anion onto the carbon atoms of benzene homocycles which result in the formation of by-products.

The presence of many reaction impurities makes it necessary to carry out chromatographic treatment to isolate pure mequitazine. Finally, the yields obtained in this way are low.

Other patents relate to the preparation of mequitazine, for example, JP-KOKAI 04 169 583 (Chem. Abstr.: 118: 6983) and JP-KOKAI 05 140 157 (Chem. Abstr.: 120: 8602) (Use of quinuclidine Spiro epoxide on a potassium derivative of phenothiazine).

While these patents are improvements on previous preparations, the problem of how to obtain a good yield of mequitazine is not resolved.

Document FR 2 777 278 describes the preparation of 3-(hydroxymethyl)quinuclidine for use as a synthesis intermediate in the preparation of mequitazine. According to this document, the starting products can be 3-(methylene)quinuclidine oxide or 3-quinuclidinone which are transformed into 3-(hydroxymethyl)quinuclidine via 3-methoxymethyl-3-quinuclidinol.

Document WO 9929692 describes a process for the synthesis of mequitazine and its levorotatory isomer. The process in question consists in reacting a lithiated derivative of phenothizaine with 3-(hydromethyl)quinuclidine mesylate. The latter product is also described as a new intermediate in the synthesis of mequitazine.

This invention puts forward a new compound as an intermediate in the synthesis of medications derived from quinuclidine, and in particular mequitazine.

This invention puts forward a process for the preparation of this new intermediate as well as a new route for the synthesis of mequitazine from this new synthesis intermediate.

To this end, this invention relates to 1-aza-bicyclo[2.2.2]oct-2-en-3-ylmethyl acetate (5) having the following formula:

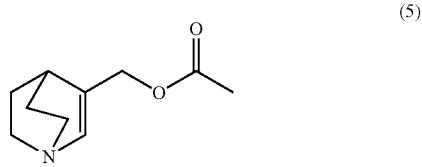

This compound has never been described in the prior art and can act as an intermediate in the synthesis of mequitazine via allylic amination with phenothiazine.

This compound (5) can be obtained from the allylic alcohol of quinuclidine, or 1-aza-bicyclo[2.2.2]oct-2-en-3-ylmethanol, (3) having the following formula:

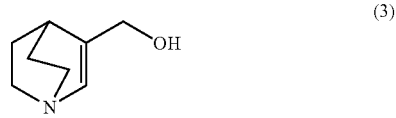

This allylic alcohol (3) has been synthesized previously via reduction of the corresponding methyl ester, itself obtained by dehydration then hydrolysis of cyanoalcohol produced from quinuclidinone (U.S. Pat. No. 4,937,239, JP 60258187, U.S. Pat. No. 4,467,095), representing 4 steps to the ester.

This invention describes two synthesis routes that are more competitive for this compound (3), each consisting of only two steps.

It can be prepared from two possible routes starting with quinuclidinone (1):

First route:

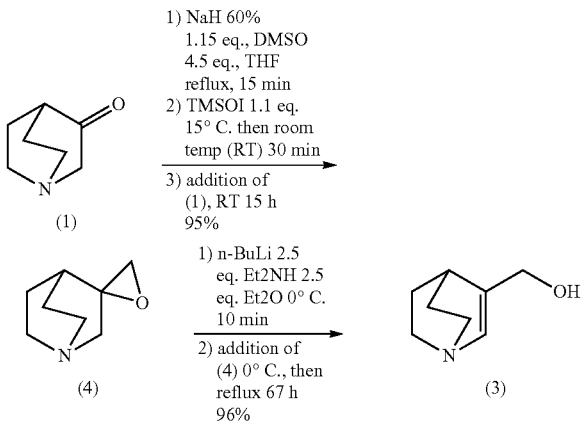

Second route:

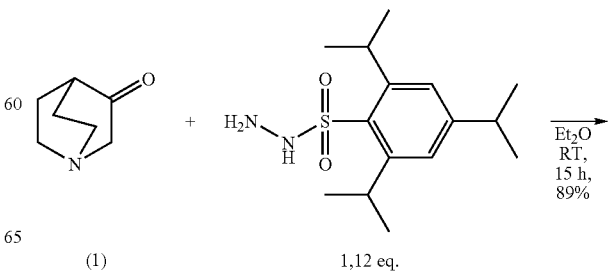

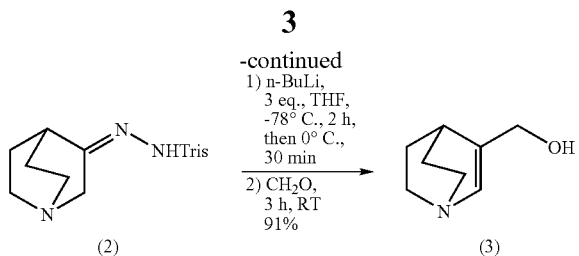

The first route consists in preparing 3-epoxyquinuclidine (4):

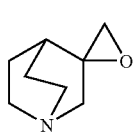

To this end, sodium hydride at 60% in oil (1.14 g, 28.5 mmoles, 1.15 eq.) is put in suspension in anhydrous tetrahydrofuran (8 ml) after which the mixture is refluxed. Dimethylsulfoxide is added leading to an intense release of hydrogen. Stirring is continued for 15 min after which the mixture is placed at 15° C. and trimethylsulfoxonium iodide (6 g, 27.26 mmoles, 1.1 eq.) is added. Stirring is continued for 30 min at room temperature. The reaction mixture becomes thicker and thicker. 3-quinuclidinone (1) (3.1 g, 24.8 mmoles, 1 eq.) dissolved in tetrahydrofuran (3 ml) is added. Heat is released and stirring is continued for 15 h. Water is then added (100 ml) and the mixture is extracted six times with chloroform. The organic phase is washed several times in water, then dried on $Na_2SO_4$, filtered and evaporated to give a yellow oil (2.3 g, 67%).

The epoxide (4) obtained in this way undergoes b-deprotonation to give compound (3) according to the following method:

n-butyllithium (1.2 ml, 1.96 mmole, 2.5 eq.) is added at 0° C. to a solution of diethylamine (0.20 ml, 1.96 mmole, 2.5 eq.) in anhydrous diethyl ether (5 ml). The mixture is stirred for 10 min, then epoxide (4) (109 mg, 0.79 mmole, 1 eq.) dissolved in diethyl ether (1 ml) is added at 0° C. The mixture is stirred under reflux for 67 h. A potassium carbonate aqueous solution is added, after which the mixture is extracted with dichloromethane and ether. The organic phases are dried on $Na_2SO_4$, filtered and evaporated to give a yellow oil (105 mg, 96%).

According to an alternative route, compound (3) can be obtained through the Shapiro reaction on hydrazone (2):

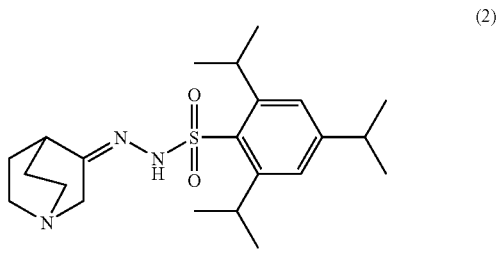

Hydrazone (2) can be obtained, starting with 3-quinuclidinone, according to the following procedure:

Triisopropyl phenyl hydrazine (20.3 g, 68 mmoles, 1.12 eq.) is dissolved in anhydrous diethyl ether (250 ml). A 3-quinuclidinone solution (1) (7.54 g, 60.3 mmoles, 1 eq.) dissolved in diethyl ether (100 ml) is cannulated at room temperature, and the mixture is stirred vigorously for 15 h. The white precipitate is filtered then washed three times in a minimum amount of diethyl ether, then dried under vacuum (21.84 g, 89%).

The Shapiro reaction on hydrazone (2) results in the allylic alcohol (3) using a method such as that described below:

Hydrazone (2) (10.26 g, 25.3 mmoles, 1 eq.) is dissolved in anhydrous tetrahydrofuran (50 ml) and placed at −78° C. n-butyllithium (47.5 ml, 76 mmoles, 3 eq.) is added over a period of 30 min. The mixture turns red and is stirred for 2 h, then placed at 0° C. Nitrogen is released for about 15 min and the mixture turns an orange-yellow colour. Paraformaldehyde (2.28 g, 76 mmoles, 3 eq.) is added at 0° C. The mixture is then stirred at room temperature for 3 h and turns a clear yellow. Water and potassium carbonate are added and the mixture is extracted with diethyl ether. The organic phases are dried on $Na_2SO_4$ and the residue is purified on silica (dichloromethane/methanol/triethylamine: methanol/triethylamine: 9/1/0.1) to give a yellow oil (6.4 g, 91%).

As mentioned earlier, compound (3) can be used in the synthesis of mequitazine via allylic substitution from the acetate derivative of (3), followed by catalytic hydrogenation of dehydromequitazine (6).

Thus, compound (5) can be obtained from the allylic alcohol (3):

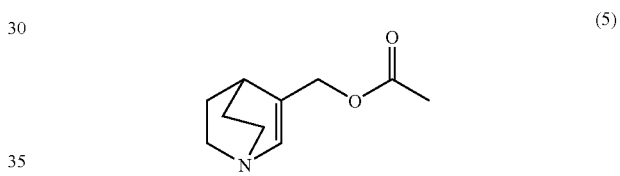

according to the following procedure:
Allylic alcohol (3) (126 mg, 0.9 mmole, 1 eq.) is placed in dichloromethane (4 ml) at 0° C. Acetic anhydride (0.1 ml, 1.1 mmole, 1.2 eq.) is added, and the mixture is then stirred for 3 h. Water is added and the phases are separated. The aqueous phase is made basic using a 10% potassium carbonate solution, then extracted with dichloromethane. The organic phases are combined, dried on $Na_2SO_4$, filtered and evaporated to give an orange oil (137.6 mg, 84%).

Compound (5) is complexed with Palladium (0) and reacted with phenothiazine to obtain dehydromequitazine (6):

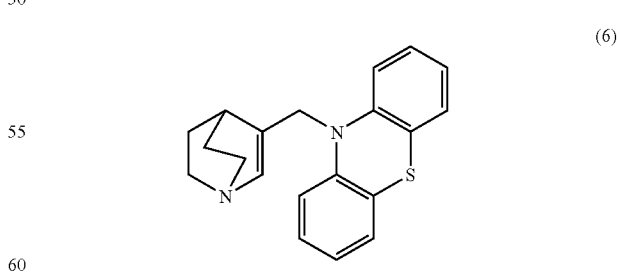

according to the following procedure:
Phenothiazine (6.6 g, 33 mmoles, 1.5 eq.) is placed in tetrahydrofuran (50 ml) at room temperature, then sodium hydride (880 mg, 36.4 mmoles, 1.65 eq.) is added. Stirring is continued for 20 min at room temperature and a dark green anion is obtained.

Preparation of the complex:

In parallel, tetrakis(triphenylphosphine)palladium (1 g, 0.66 mmole, 4%) is added to the acetate (5) (4 g, 22 mmoles, 1 eq.) in solution in tetrahydrofuran (50 ml). The mixture is stirred at room temperature for 10-15 min (red complex).

The previously formed complex is cannulated on the anion and the mixture is stirred for 3 h. A saturated aqueous potassium carbonate solution is added and the mixture is extracted with dichloromethane. The organic phases are dried on $Na_2SO_4$, filtered and evaporated. The resulting green oil is purified on silica dichloromethane/methanol/triethylamine: 96/4/0.5) and a beige solid is obtained (4 g, 58%).

Dehydromequitazine (6) then undergoes catalytic hydrogenation according to the following procedure:

Dehydromequitazine (6) (51 mg, 0.16 mmole, 1 eq.) is dissolved in degassed anhydrous methanol (2 ml) and degassed anhydrous toluene (1 ml). The mixture is then cannulated in a reactor previously purged three times in vacuum/argon. The Pd/C catalyst (5 mg, 10% by mass) is added, then the reactor is placed under $H_2$, purged three times at 5 bar of $H_2$, then placed under 100 bar and stirred for 24 h. Activated carbon is added, and the mixture is filtered on Celite then evaporated to give a yellow oil (47 mg, 91%).

Mequitazine (7) is thus obtained in a racemic form:

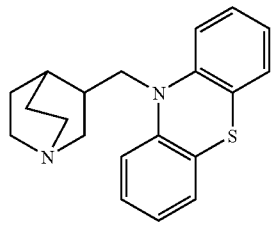

(7)

A general overview of the methods of obtaining mequitazine (7), allylic alcohol (3) and compound (5) is given below:

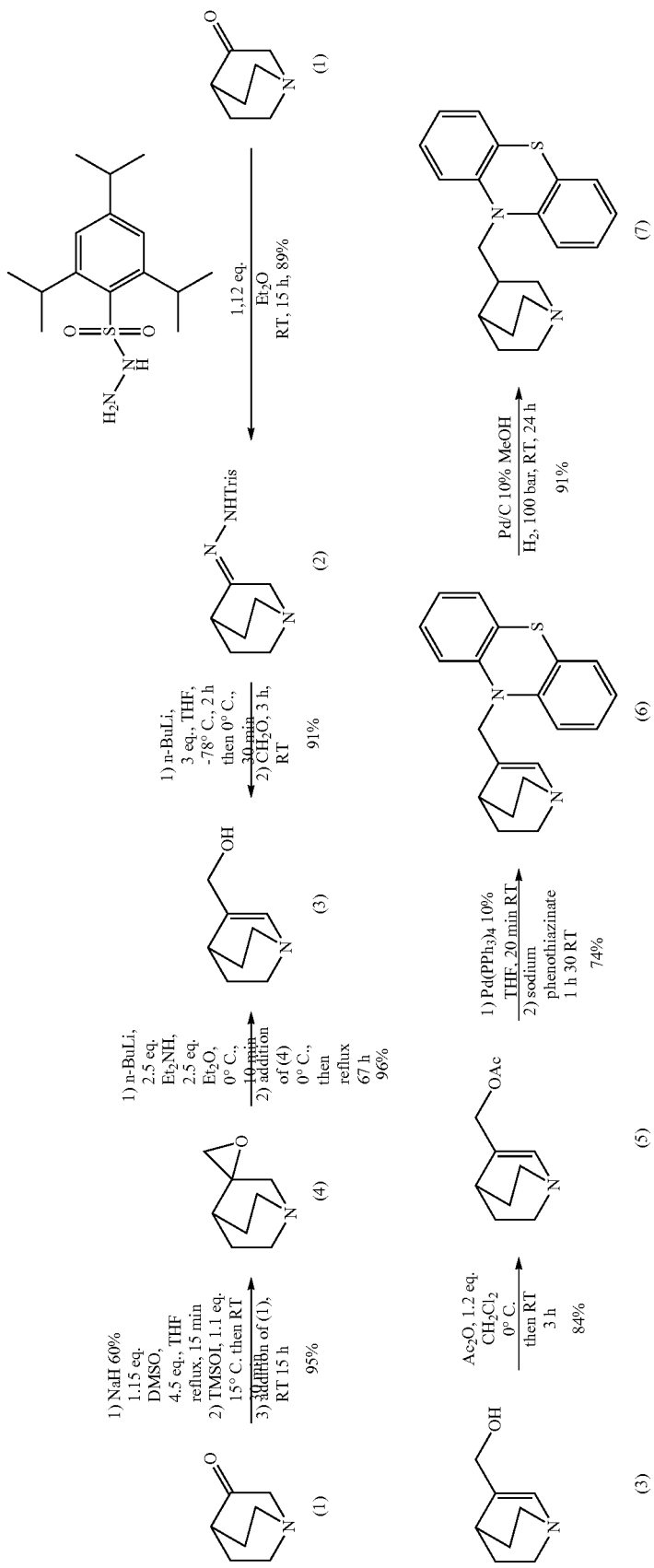

These preparation processes involve only a limited number of synthesis steps, present good yields and can be industrialized.

The invention also relates to a process for the preparation of mequitazine by using 1-aza-bicyclo[2.2.2]oct-2-en-3-ylmethyl acetate (5).

Mequitazine obtained according to the procedure described here is in the form of a racemic mixture. If the target is to obtain the levorotatory isomer as described in FR 2 522 660, enantiomer-selective catalytic hydrogenation of dehydromequitazine is necessary. This enantiomer-selective catalytic hydrogenation can be performed with an ML* type catalyst in which M represents a transition metal such as ruthenium or rhodium and L is a chiral ligand, for example (R,R)Rh(cod) (DIPAMP) BF$_4$.

The invention claimed is:

1. Process for the manufacture of mequitazine of formula (7)

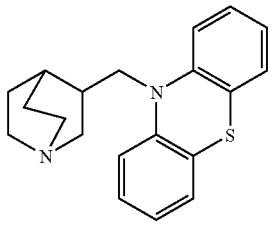

(7)

in the form of a racemic mixture or an optic isomer mixtures in all proportions, using 1-aza-bicyclo [2.2.2]oct-2-en-3-yl-methyl acetate of the formula (5) as a synthesis intermediate.

2. Process for the manufacture of mequitazine of formula (7)

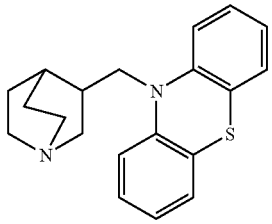

(7)

involving the following reaction sequence:
(i) complexing of palladium acetate (5);

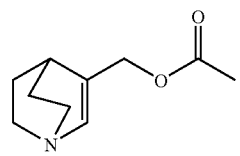

(5)

(ii) followed by an allylic amination reaction with phenothiazine leading to dihydromequitazine of formula (6);

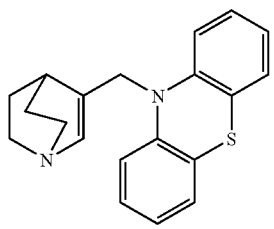

(6)

(iii) the latter being subjected to catalytic hydrogenation leading to mequitazine of formula (7);

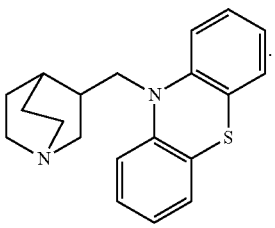

(7)

3. Process according to claim 2, wherein catalytic hydrogenation is carried out under enantiomer-selective conditions.

4. Process according to claim 2, wherein mequitazine is in the form of a pure levorotatory isomer or pure dextrototatory isomer.

* * * * *